United States Patent [19]

Satoh

[11] Patent Number: 5,051,406
[45] Date of Patent: Sep. 24, 1991

[54] PHARMACEUTICAL COMPOSITION USING ALBUMIN AS A CARRIER AND PROCESS FOR PRODUCING THE SAME

[75] Inventor: Toshio Satoh, Tokushima, Japan

[73] Assignee: Nippon Hypox Laboratories Incorporated, Tokyo, Japan

[21] Appl. No.: 620,394

[22] PCT Filed: Mar. 4, 1988

[86] PCT No.: PCT/JP88/00237
§ 371 Date: Oct. 17, 1988
§ 102(e) Date: Oct. 17, 1988

[87] PCT Pub. No.: WO88/06457
PCT Pub. Date: Sep. 7, 1988

Related U.S. Application Data

[63] Continuation of Ser. No. 265,455, Oct. 17, 1988, abandoned.

[30] Foreign Application Priority Data

Mar. 4, 1987 [JP] Japan .................................. 62-49135
Mar. 4, 1987 [JP] Japan .................................. 62-49136

[51] Int. Cl.$^5$ ..................... A61K 47/42; A61K 37/00; A61K 31/00
[52] U.S. Cl. ..................................... 514/21; 530/362; 530/363; 514/776
[58] Field of Search ................... 514/776, 21; 530/362, 530/363

[56] References Cited

U.S. PATENT DOCUMENTS 3,933,996  1/1976  Charlton ............................... 514/21
4,578,391  3/1986  Kawata et al. ...................... 514/256
4,702,918  10/1987  Ushimaru et al. .................. 514/560

FOREIGN PATENT DOCUMENTS 108020  7/1982  Japan .

OTHER PUBLICATIONS

Asano et al., Kokai publication, No. 57-106610, 7/2/82.
Freedman; J. Kokai Pat. No. Sho 62(1987)-207217.
Fujoka et al., 61-236729 (A), JP.
Kuwayama et al., 57-108020 JP.
Kikazawa et al., 57-26615 JP.
Kaetsu et al., 56-115713 JP.

Primary Examiner—Howard E. Schain
Assistant Examiner—Choon Koh
Attorney, Agent, or Firm—Nixon & Vanderhye

[57] ABSTRACT

The pharmaceutical composition of the present invention is a pharmaceutical composition of high drug content containing 1-200 parts by weight of a drug having a protein binding property and 100 parts by weight of albumin.

This pharmaceutical composition is produced by stirring the drug and albumin of the above proportions at a high speed in an aqueous solvent and then removing the solvent by distillation, and has effects of alleviating the side effect of the drug used therein and also of improving the absorption, light stability, etc. of the drug.

6 Claims, 6 Drawing Sheets

FIG. 2

A : NIFEDIPINE-ALBUMIN COMPOSITION
B : NIFEDIPINE POWDER
C : NIFEDIPINE GRANULE
D : ALBUMIN

○ : dl-α-TOCPHEROL ALONE

● : dl-α-TOCOPHEROL- EGG ALBUMIN (1:5)

△ : dl-α-TOCOPHEROL-STEARIC ACID-
    EGG ALBUMIN (1:0.5:5)

PHARMACEUTICAL COMPOSITION USING ALBUMIN AS A CARRIER AND PROCESS FOR PRODUCING THE SAME

CROSS-REFERENCE TO RELATED APPLICATION

This is a continuation of earlier application Ser. No. 07/265,455 filed Oct. 17, 1988, now abandoned.

TECHNICAL FIELD

The present invention relates to a pharmaceutical composition using albumin as a carrier, as well as to a process for producing the pharmaceutical composition. More particularly, the present invention relates to a pharmaceutical composition wherein the side effect undesirable to the human body, of the drug contained therein has been alleviated and further the absorption, light stability, etc. of the drug has been improved, as well as to a process for producing the pharmaceutical composition.

BACKGROUND ART

For the alleviation of the side effect of drugs, there have been proposed pharmaceutical compositions comprising a drug and a carrier or the like. As an example, non-steroidal anti-inflammatory agents show a strong anti-inflammatory action to inflamation-affected parts, but they are known to give serious side effects to the central nervous system and the digestive system and to cause hemorrhage and ulcer in the digestive system, in particular; in order to alleviate these side effects, there was proposed, for example, a pharmaceutical composition comprising a non-steroidal anti-inflammatory agent or a salt thereof and 0.2–50 parts by weight, based on 1 part by weight of the former, of salicylic acid and/or an alkali metal salicylate as an activating agent [Japanese Patent Application Kokai (Laid-Open) No. 82715/1976). Further, it was proposed to include Indometacin, a non-steroidal anti-inflammatory agent in a biodegradable carrier selected from collagen and gelatin (Japanese Patent Application Kokai (Laid-Open) No. 84213/1985), or to include Indometacin in cyclodextrin to enable the sustained release of Indometacin (Japanese Patent Application Kokai (Laid-Open) Nos. 62313/1979 and 117018/1979). Furthermore, there was proposed in Japanese Patent Application Kokai (Laid-Open) No. 110334/1979 a method wherein Indometacin is mixed with a benzodiazepine compound to thereby reduce the administration amount of Indometacin and to inhibit the expression of its serious side effect.

Though these conventional methods are superior in sustained release of drug, they are poor in absorption of drug into human body, take a long time before the drug exhibits an anti-inflammatory action, and hardly show sufficient effects for the alleviation of the side effect of the drug to the digestive system.

There were also proposed pharmaceutical compositions using albumin as a carrier, such as a composite of a 5-fluorouracil derivative and albumin [Japanese Patent Application Kokai (Laid-Open) No. 151988/1979) and a drug-albumin composite of sustained release type (Japanese Patent Application Kokai (Laid-Open) No. 162595/1983). These pharmaceutical compositions using albumin as a carrier described in the above patent documents, however, have drawbacks in that in their preparation, the binding property of the carrier albumin must be improved in advance at a pH of 6-11 at a temperature of 30° C. or below using a cyanogen halide or a perhalogenic acid, or the affinity of the carrier albumin must be improved in advance using a spacer of a functional compound or the like, thus requiring many preparation steps and making the preparation procedure complex.

The present invention has been made in order to solve the above-mentioned problems of prior arts. The first object of the present invention is to provide a pharmaceutical composition which can alleviate the side effect of the drug contained therein to the skin and mucous membrane, particularly the digestive system and can improve the absorption, light stability, etc. of the drug. The second object of the present invention is to provide a process which can produce a pharmaceutical composition having the above advantages according to a simple procedure.

DISCLOSURE OF THE INVENTION

The present invention has been made in order to achieve the above objects. The present invention relates to a pharmaceutical composition of high drug content characterized by containing 1–200 parts by weight of a drug having a protein binding property and 100 parts by weight of albumin.

The present invention also relates to a process for producing a pharmaceutical composition of high drug content, characterized by stirring 1–200 parts by weight of a drug having a protein binding property and 100 parts by weight of albumin at a high speed in an aqueous solvent and than removing the solvent.

BEST MODE FOR CARRYING OUT THE INVENTION

The pharmaceutical composition of the present invention is a pharmaceutical composition of high drug content containing 1–200 parts by weight of a drug having a protein binding property and 100 parts by weight of albumin.

Japanese Patent Application Kokai (Laid-Open) No. 216126/1983 describes the use of human serum albumin in order to make water-soluble a drug having no or very low solubility in water. The solubilization method described in the above patent document, however, is the application of the conventionally known method for measurement of the protein binding ratio of a drug; in this method, a drug can be solubilized only in a very small amount of about 0.01-0.8% based on the serum albumin; accordingly, the method is exceptionally useful only when a drug is used at a very low dosage as in the case of Prostaglandin shown in the above patent document.

In contrast, the pharmaceutical composition of the present invention using natural albumin as a carrier can contain a drug in a high concentration as described in detail below and accordingly can be applied even to ordinary drugs of high administration dosage. Hence, the present pharmaceutical composition is entirely different from that described in the above patent document.

As the albumin used in the present invention, there can be mentioned, for example, egg albumin, serum albumin, plakalbumin, α-lactalbumin, leucosin, phaselin and Revmerine. Of these, egg albumin is especially preferred. The use of a human-derived albumin is preferred when the present composition is applied to drugs requiring antigenicity. It is preferred that the drug used in the present invention has a protein binding ratio of at least 10%, preferably at least 20%. The drug is used in an amount of 1-200 parts by weight, particularly 5-200 parts by weight based on 100 parts by weight of albumin.

Specific examples of the drug used in the present invention are as follows. As non-steroidal anti-inflammatory agents, there can be mentioned Aspirin, Ibuprofen, Alclofenac, Indomethacin, Mefenamic Acid, Flufenamic Acid, Sulindac, Piroxicam, Diclofenac, Diclofenac sodium, Tiaramide, Tolmetin, Phenylbutazone, Naproxen, etc.; as steroidal anti-inflammatory agents, Predonisolone, Triamcinolone, Dexamethasone, Beclometasone, Hydrocortison, etc.; as ataraxics, Chlorpromazine hydrochloride, Carbamazepine, Clonazepam, Phenitoin, Haloperidol, Chlordiazepoxide, Mexazolam, Amitriptyline hydrochloride, Imipramine hydrochloride, Flunitrazepam, Triazolam, etc.; as hypotensive diuretice, Furosemide, Ethacrynic acid, Bumetanide, Hydrochlorothiazide, Trichlormethiazide, Metolazone, Chlortalidone, etc.; as antihypertensive agents, Prazosin hydroctloride, Reserpin, Labetalol, Clonidine hydrochloride, Bunazocine hydrochloride, Captopril, Hydralazine hydrochloride, Budralazine, etc.; as cardiovascular agents, Theophyline, Etilefrine hydrochloride, Dobutamine hydrochloride, Quinidine sulfate, Lidocaine, Mexiletine hydrochloride, Digitoxin, Digoxine, Deslanoside, Vinpocetine, Cinepazide maleate, etc.; as coronary vasodilators, Diltiazem hydrochloride, Nifedipine, Verapamil hydrochloride, Nicardipine hydrochloride, Isosorbide dinitrate, Nitroglycerine, etc.; as sympathomimetic agents, Isoprenaline hydrochloride, etc.; as peripheral muscle relaxants, Eperisone hydrochloride, Dantrolene, Buclofen, etc.; as ischemic heart disease agents, Dilazep dihydrochloride, Dipyridamole, Nicorandil, etc.; as β-stimulants, Etilefrine hydrochloride, Dobutamine hydrochloride, etc.; as β-blockers, Alprenolol hydrochloride, Propranolol hydrochloride, Oxprenolol hydrochloride, Pindolol, etc.; as antispamedics, Atoropin, Scopolamine, etc.; as antibiotics, Cefaclor, Cefalexin, Froxacine, Pipemidic acid, Sulfamethoxazolin sodium, Cefmenoxime hemihydrochloride, Cefoxitin sodium, Ceftizoxime sodium, Latamoxef sodium, Ampicillin, Sulbenicillin disodium, Benzylpenicillin potassium, Phenoxymethylpenicillin potassium, Chlortetracycline hydrochloride, Tetracycline hydrochloride, Minocycline hydrochloride, Doxycycline hydrochloride, Rifampicin, Erythromycin, Clindamycin, etc.; as antifungal agents, Griseofulvin, Nystatin, Amphotericin B, Miconazole, etc.; as chemotherapeutics, Nalidixic acid, Enoxarin, Ozole, etc.; as antivirotic agents, Vidarabine, etc.; as antineoplastic agents, Methotrexate, Vindesine sulfate, Vincristine sulfate, Daunorubicin hydrochloride, etc.; as an anti-ulcerous drug, Cetraxate hydrochloride, Cimetidine, Famotidine, Pirenzepine hydrochloride, Ranitidine hydrochloride, Sulpiride, etc.; as antiallergic agents, Ketotifin, Tranilast, Azelastin, Chlorpheniramine maleate, Clemastine fumarate, Mequitazine, etc.; as expectorants, Ambroxol hydrochloride, etc.; as vitamines, Calcitriol, Tocopherol, Tocopherol acetate, Tocopherol nicotinate, Riboflavine, Folic acid, Menadione, Phytonadione, etc.; as hepatonics, Malotilate, Glycyrrhizin, etc.; as diabetic agents, Acetohexamide, Chlorpropamide, Tolbutamide, etc.; as hormones, Danazol, Levothyroxine, Liothyronine, Propylthiouracil, etc.; as uricosuric agents, Probenecid, etc.; as immunosuppressants, Azathioprine, Cyclosporin, etc.; and as antiemetics, Domperidone, etc.

The pharmaceutical composition of the present invention can contain a fatty oil and/or a fatty acid together with the above-mentioned albumin and drug. As the fatty oil, there can be mentioned olive oil, corn oil, coconut oil, soybean oil, sesame oil, etc. As the fatty acid, thera can be mentioned straight chain fatty acids of 8-30 carbon atoms. The addition of the fatty oil and-/or the fatty acid further increases the already improved drug absorption of the present composition.

When the composition of the present invention is used as a medicine, it can be produced into various forms suitable for oral administration. The composition of the present invention can be produced into, for example, a medicine containing the composition and a nontoxic pharmaceutically acceptable carrier used in ordinary medicines. Such a medicine can be prepared in any of a solid form (e.g. tablets, capsules, grains, powder, parvules, sugar coated tablets, troches), a semisolid form (e.g. ointment, cataplasma, cream, suppository) and a liquid form (e.g. emulsion, suspension, lotion, tincture, spray, syrup) depending upon the application. As the nontoxic pharmaceutically acceptable carrier usable in the present invention, there can be mentioned, for example, starch, gelatin, glucose, lactose, fructose, maltose, magnesium carbonate, talc, magnesium stearate, methyl cellulose, carboxymethyl cellulose or its salts, gum arabi, polyalkylene glycol, alkyl p-hydroxybenzoates, single syrup, ethanol, propylene glycol, glycerol, vaseline and carbowax.

The above medicine can further contain therapeutically useful other drugs, a dispersing agent, an antioxidant, a preservative, a stabilizer, a flavoring agent, a binder, a lubricant, etc.

The content of the composition of the present invention in the medicine differs by the form of medicine. However, it is generally desirable that the active compound of the composition be contained in the medicine in a concentration of 5-100 % by weight when the medicine takes a solid or semisolid form and in a concentration of 0.1-10% by weight when the medicine takes a liquid form.

Next, the process for producing the pharmaceutical composition of the present invention is explained. In the process for producing the pharmaceutical composition of the present invention, at first, a step is effected in which 100 parts by weight of albumin and 1-200 parts by weight of a drug having a protein binding property are stirred at a high speed in an aqueous solvent.

The aqueous solvent can be any as long as it can dissolve albumin without denaturing it, tut water is most preferred. Part of water can be replaced by a hydrophilic solvent such as methanol, ethanol, acetore, ethyl acetate or the like. It is also possible to use, together with water and the hydrophilic solvent, a hydrophobic solvent such as chloroform, dichloroethane, benzene or the like. When the drug has no or very low solubility in water, it is preferable that the drug be dissolved in the above organic solvent and the resulting drug solution be added to an aqueous albumin suspension. In this case, the concentration of albumin in the aqueous suspension is not particularly restricted but is at least 1% by weight, preferably 2-25% by weight. In that case, the concentration of the drug in the organic solvent is not particularly restricted, either, but is at least 0.1% by weight, preferably 1-50% by weight. Further, the mixing ratio of the drug solution to the albumin suspension is not particularly restricted, but it is preferable that 1-400 volumes of the drug solution be mixed with 100 volumes of the albumin suspension.

As mentioned previously, a fatty oil and/or a fatty acid can be used with both albumin and the drug. In this case, it is preferred that the drug be dissolved in the fatty oil and/or the fatty acid in a former/latter volume ratio of maximum 100/100, preferably 1/100 to 50/100 and then the resulting solution be added to an aqueous albumin suspension. Preferably, the dissolution of the drug in the fatty oil and/or the fatty acid is effected using an organic solvent. As the organic solvent, there can be used acetone, methanol, ethanol, chloroform, ethyl acetate, benzene, ether, dichloromethane, tetrahydrofuran, etc.

The temperature and time employed in the high speed stirring is not critical. Generally, there are employed 1-30 hours at temperatures at which albumin causes no thermal denaturation, preferably 4-30° C. The reaction is advantageously effected under high speed stirring. The high speed stirring is preferably effected at about 5,000-40,000 rpm using, for example, Biomixer BM-4 (product of Nihon Seiki Seisakusho, maximum revolution=30,000 rpm) or a large-sized homogenizer (product of Nichion Irikakikai Seisakusho, maximum revolution=20,000 rpm).

In the process for producing the pharmaceutical composition of the present invention, there is next effected a step in which the uniform suspension obtained in the above high speed stirring step is subjected to distillation to remove the solvent.

The removal of the solvent by distillation is conducted using a means such as air drying, vacuum drying, drum drying, spray drying, freeze drying or the like.

The resulting pharmaceutical composition of powdery state contains a drug of an amount as large as 1-200 parts by weight in 100 parts by weight of albumin and is a pharmaceutical composition of high drug content. It is a novel composition because there has hitherto existed no pharmaceutical composition in which albumin supports such a high concentration of a drug.

In the production of the composition of the present invention, it is unnecessary to use a solubilizing agent such as carboxymethyl cellulose, gum arabi, dimethylformamide, dimethyl sulfoxide or the like, or to use a surfactant which is employed in the production of albumin spherules; accordingly, there is no fear of the side effect caused by the inclusion of a solubilizing agent or a surfactant in drug-albumin compositions.

In the pharmaceutical composition of the present invention obtained according to the above process, the drug and albumin form a hydrophobic bond at least partially. The Examples which appear later confirmed that the present composition, when it is a hydrophobic bonded substance produced by, for example, spray drying, has a stereostructure having a shape of connected donuts and an average particle diameter of 5-10 $\mu$m and, when it is a hydrophobic bonded substance produced by freeze drying, has a stereostructure consisting of layered plate crystals each of 5-10 $\mu$m in average size, according to the analysis by scanning type electron micrograph.

Next, the effects of side effect alleviation, absorption improvement, light stability improvement, etc. possessed by the pharmaceutical composition of the present invention are illustrated by the following test results.

Test for absorption of nalidixic acid-albumin composition by gastrointestinal tract It was made clear from the following test that the nalidixic acid-albumin composition (nalidixic acid content: 8.9%) obtained according to the present invention improves the absorption of nalidixic acid administered after meals.

Test animal
  Male rats of Wistar strain each weighing about 290 g obtained from Sankyo Labo. were used under a satiety condition.
Composition administration and blood drawing
  The administration amount was 50 mg/kg in terms of nalidixic acid. A composition was administered in a form of its suspension in 1 ml of water, using an oral sonde. About 0.2 ml of blood was drawn from the eyeground of rat using a capillary (Drummond, 0.1 ml) and then centrifuged to obtain a serum.
Sample treatment and determination method
  The serum was mixed with an equal volume of methanol to deproteinize the serum. The determination for the deproteinized serum was conducted according to high performance liquid chromatography.
Determination conditions
  Column: ODS-80TM manufactured by TOYO SODA, 4.6 mm×15 cm
  Mobile phase: Acetonitrile: 50 mM citric acid solution: 1 M ammonium acetate =35 : 64 : 1
  Flow rate: 0.7 ml/min
  Detection wavelength: 258 nm
  Injection amount: 10 $\mu$l
  Column temperature: Room temperature
  The calibration curve was obtained by adding known nalidixic acid to a blank serum and subjecting the mixture to the same procedure as for the sample.
  The results are shown in Table 1.

As is clear from Table 1, when the nalidixic acid-albumin composition was administered in an amount of 50 mg/kg in terms of nalidixic acid, the blood concentration of nalidixic acid reached the maximum in 1.5 hours after the administration and the concentration at that time was calculated to be about 25 $\mu$g/ml. In contrast, when a nalidixic acid powder was administered in the same amount, the blood concentration reached the maximum in 3 hours after the administration and the concentration at that time was calculated to be about 7 $\mu$g. The area below the blood concentration-time curve (AUC) between 0 and 8 hours was calculated for each administration case. The area was 108.9 μg.hr/ml for the composition and 34.6 μg.hr/ml for the nalidixic acid powder. From the comparison of these pharmacokinetic parameters, it can be concluded that the absorption of the nalidixic acid-albumin composition of the present invention is superior to that of the nalidixic acid powder. In general, when a drug is adsorbed by or bonded to a carrier and is administered in the resulting composition form, the drug is released sustainedly and is absorbed at a slower rate; however, in the composition of the present invention, nalidixic acid absorption is faster than the absorption of the nalidixic acid powder as clearly seen in Table 1. This is a characteristic effect of the composition of the present invention.

Test for formation of stomach ulcer by Indometacin-albumin composition

It is known that while non-steroidal anti-inflammatory agents show a strong anti-inflammatory action to inflammation-affected parts, they cause hemorrhage and ulcer to the digestive system. It was made clear from the following test that the Indometacin-albumin composition (Indometacin content: 8.8%) obtained according to the present invention shows no ulcer formation inherent to Indometacin as a non-steroidal anti-inflammatory agent and yet expresses an anti-inflammatory action equivalent to that of Indometacin.

The test was conducted according to the method by Okabe et al. (J. Jap. Pharmacol. Vol. 29, 670 (1979)). That is, two groups of male rats of Wistar strain each weighing 180–200 g (one group consisted of 8 such rats) were fasted for about 18 hours. As test samples, there were used suspensions obtained by suspending the Indometacin-albumin composition (Indometacin 3 g albumin 30 g) obtained in Example 23 or 24 (described later) in a 1% carboxymethyl cellulose sodium solution (hereinafter referred to as 1% CMCNa) in an amount of 20 mg/kg in terms of Indometacin. These suspensions were orally administered to the rats at a proportion of 0.5 ml/100 g (rat). As a control sample, a suspension obtained by suspending an Indometacin powder in 1% CMCNa in an amount of 20 mg/kg was administered similarly. After 7 hours from the administration, all the rats were sacrificed under etherization. 8 ml of a 1% aqueous buffered formalin solution was injected into the stomach of each rat. Then, the stomach was enucleated and immersed in a 1% aqueous buffered formalin solution for 15 minutes. Thereafter, the stomach was incised along the greater curvature and the lesioned portions (ulcer portions) generated in the mucous membrane were measured for their major axes (mm) under a stereoscopic microscope. The total of the major axes was taken as an ulcer index.

The results are shown in Table 1.

TABLE 1

| Sample | Ulcer index (Mean ± S.E.) | Incidence |
|---|---|---|
| Indometacin-egg albumin composition of Example 23 (containing 20 mg/kg in terms of Indometacin) | 93.3 ± 38.5 | 27.3% |
| Indometacin-egg albumin composition of Example 24 (containing 20 mg/kg in terms of Indometacin) | 115.3 ± 22.6 | 33.7% |
| Indometacin powder 20 mg/kg | 341.7 ± 49.9 | 100.0% |

As is seen from Table 1, the ulcer incidences in stomach mucous membrane, of the Indometacin-egg albumin compositions of Examples 23 and 24 were apparently lower than that of the Indometacin powder. These Indometacin-egg albumin compositions gave no side effect in other digestive organs, either.

Anti-inflammatory action of Indometacin-albumin composition

The anti-inflammatory action of the Indometacin-albumin composition can also be proven by the following test by carragheenin induced plantar edema method.

A wide-mouthed glass container filled with water was placed on an electronic even balance. Into the water was immersed the sole of the right hind leg of rat up to the borders of the hair, and the resulting weight increase was measured to obtain a volume of the sole.

Three groups of male rats of Wistar strain each weighing 150–180 g (one group consisted of 6 such rats) were fasted for 18 hours and then measured for their sole volumes. These volumes were each taken as a sole volume before administration.

As test samples, there were used two suspensions, i.e. a suspension obtained by suspending the Indometacin-egg albumin composition (Indometacin 3 g / egg albumin 30 g) obtained in Example 24 (described later) in 1% CMCNa in an amount of about 5 mg/kg in terms of Indometacin and a suspension obtained by suspending an Indometacin powder in 1% CMCNa in an amount of 5 mg/kg in terms of Indometacin. These suspensions were orally administered to two sample groups at a proportion of 0.5 ml/100 g (rat). At 30 minutes after the oral administration, 0.1 ml of a physiological saline solution containing 1% of λ-carragheenin was subcutaneously administered to each rat at the sole of right hind leg and, immediately, 5 ml of water was administered orally. In 1, 3 and 5 hours after the administration of the 1% λ-carragheenin solution, the sole volume of each rat was measured. Then, the swelling percent of each individual rat, the average swelling percent of each group and the corresponding inhibition ratio were calculated according to the following formulae.

As a control sample, there was used 1% CMCNa, and it was orally administered to one control group at a proportion of 0.5 ml/100 g (rat). The results were compared with those of the sample-administered groups.

Swelling percent (%) = ((B − A) ÷ A) × 100

Inhibition ratio (%) = ((C − D) ÷ C) × 100

A: Sole volume before administration
B: Sole volume after administration
C: Average swelling percent of control group
D: Average swelling percent of sample group The results are shown in the following Table 2.

TABLE 2

| Sample | Test item | 1 hr | 3 hr | 5 hr |
|---|---|---|---|---|
| Indometacin-albumin composition of Example 24 (containing 5 mg/kg in terms of Indometacin) | Swelling percent | 7.4% | 7.2% | 5.1% |
|  | Inhibition ratio | 56.5% | 59.3% | 76.3% |
| Indometacin powder (5 mg/kg) | Swelling percent | 10.3% | 8.4% | 8.5% |
|  | Inhibition ratio | 39.4% | 52.5% | 60.5% |
| 1% CMCNa | Swelling percent | 17.0% | 17.7% | 21.5% |

As is clear from Table 2, the Indometacin-albumin composition of Example 24 shows a high inhibition ratio as early as only at 1 hour after the administration, as compared with the Indometacin powder and exhibits a very high inhibition ratio even at 5 hours after the administration.

Test for light stability of Nifedipine-albumin composition

The excellency of the light stability of a Nifedipine-albumin composition is proven by the following test.

Figure 1:
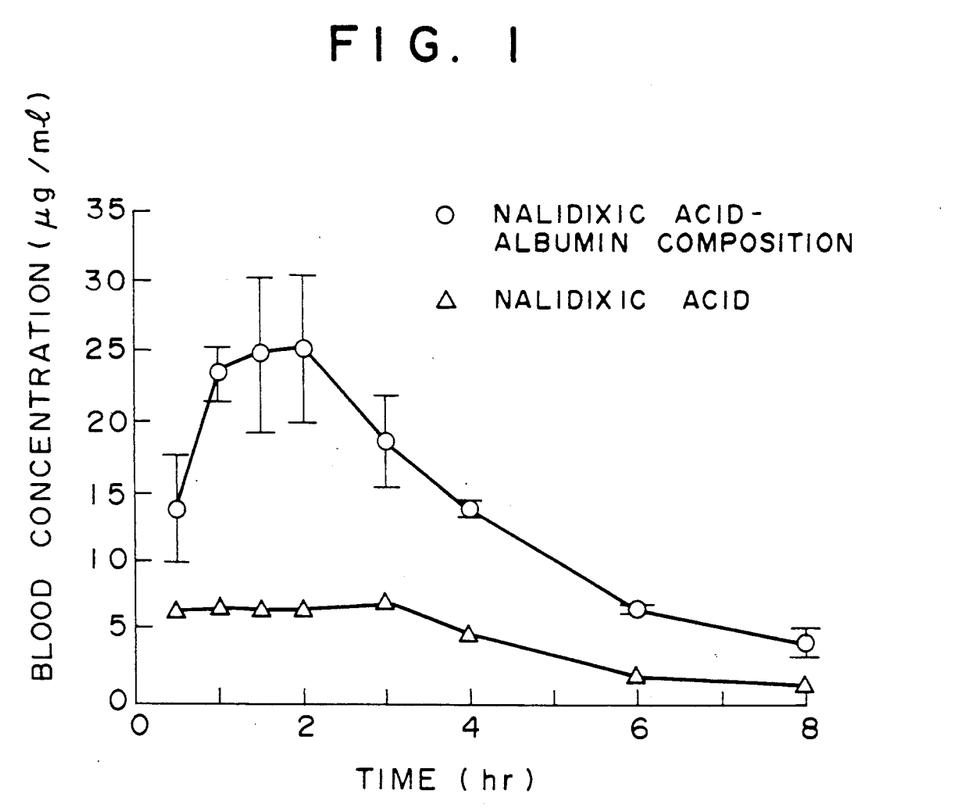
FIG. 1 is a graph showing a change with time of blood concentration of nalidixic acid after the administration of a nalidixic acid-albumin composition.
Figure 2:
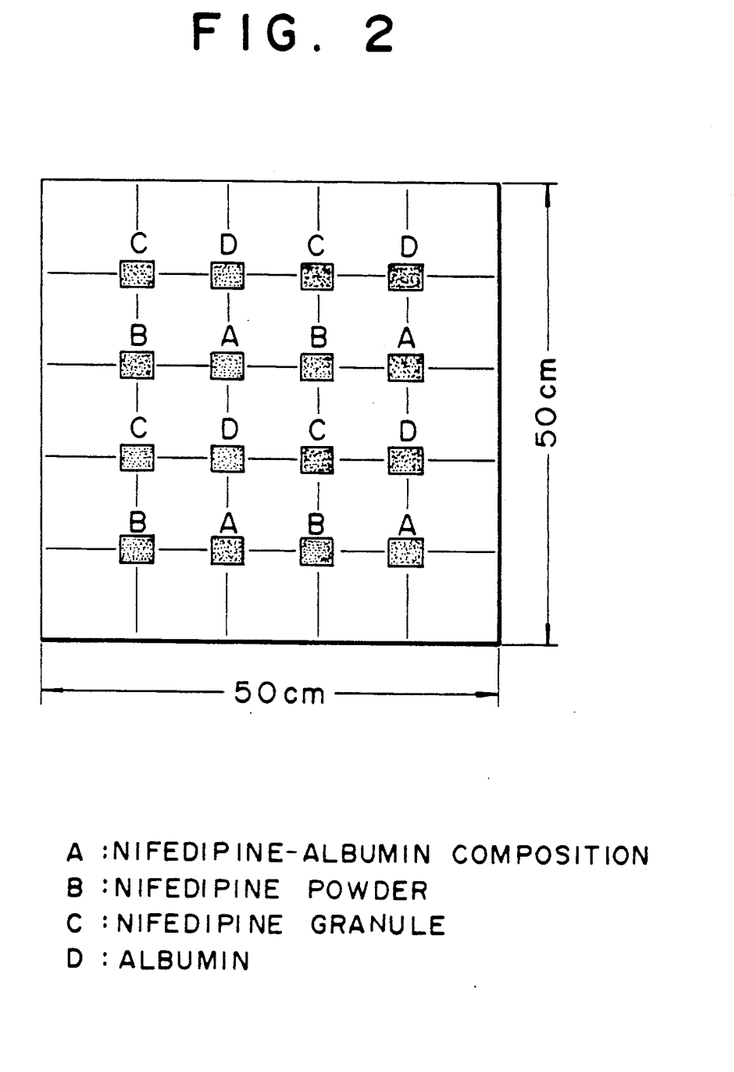
FIG. 2 is a drawing showing a flat plate used for placing thereon various samples such as a Nifedipine-albumin composition and the like and testing their light stabilities.

About 0.1 g of a Nifedipine-albumin composition containing about 0.01 g of Nifedipine, 0.1 g of a Nifedipine powder (a control) and about 0.01 g of commercially available Nifedipine granules containing about 0.001 g of Nifedipine (another control) were spread on a flat plate (50 cm×50 cm) as shown in FIG. 2 at intervals of 10 cm so as to each form a spot of 2 cm×2 cm. The plate was covered with a wooden box and allowed to stand for 24 hours while lighting a fluorescent lamp (product of TOSHIBA CORP., 10 W) provided at the center of the plate. At the start of the test, the room temperature was 12° C. and the relative humidity was 30% At the end of the test, the room temperature was 19° C. and the relative humidity was 25%.

After the light irradiation, each test sample was recovered by spot and weighed accurately. Then, 10 ml of methanol was added An ultrasonic wave was applied to each mixture for 30 minutes using an ultrasonic cleaner (high frequency output 150 W, 28 kHz). The impurities were removed by filtration and the residue on the funnel was washed with methanol. The filtrate and the washings were combined and the mixture was adjusted accurately to 50 ml with methanol to obtain three test sample solutions. About 100 ml each of the same Nifedipine-albumin composition, the same Nifedipine powder and the same commercially available Nifedipine granules were stored in the same manner with the lamp shielded. Each of them was then weighed accurately. 19 ml of methanol was adjusted to each sample and the subsequent procedure was conducted in the same manner to obtain three control solutions. With respect to the Nifedipine powder, both the control solution and the test sample solution were further diluted accurately to a 10-fold volume. A given amount of each of the control solutions and the test sample solutions was accurately injected into a high performance liquid chromatograph column to determine the concentration of Nifedipine. This determination was conducted using a calibration curve obtained by subjecting two Nifedipine standard solutions of known but different Nifedipine concentrations to the simultaneous analysis. The analytical conditions in high performance liquid chromatography were as follows.

Column: Waters-type Novapack C18
Mobile phase: 55% methanol
Flow rate: 1 ml/min
Detection wavelength: 350 nm The residue percent was calculated from the following formula.

Residue percent=((Test sample solution concentration)/(test sample weight) (mg))÷((control solution concentration)/(test sample weight) (mg))×100

The results are shown in Table 3.

TABLE 3

| Sample | Residue percent of Nifedipine (average) |
|---|---|
| Nifedipine-albumin composition | 64.6% |
|  | (number of test samples: 4) |
| Nifedipine powder | 30.2% |
|  | (number of test samples: 4) |
| Commercially available Nifedipine granules | 40.6% |
|  | (number of test samples: 4) |

As is clear from Table 3, the Nifedipine-albumin composition suppressed the light decomposition of Nifedipine contained therein and had a higher light stability than the commercially available Nifedipine granules This stability can be further improved by processing the above composition into an ordinary medicine.

Test for absorption characteristic of Tocopherol-egg albumin composition

The excellency of a fat-soluble vitamine dl-α-Tocpherolegg albumin composition (this is one of the compositions of the present invention) in absorption characteristic is proven by the following test.

dl-α-Tocopherol alone and a dl-α-Tocopherol-egg albumin composition were packed in two No. 00 capsules in an amount of 100 mg in terms of dl-α-Tocopherol. The capsules were orally administered to dogs. At 3, 6, 9, 12, 24 and 36 hours after the oral administration, blood was drawn from the leg vein of each dog and centrifuged to obtain a serum. To 0.5 ml of the serum were added 1 ml of methanol and 6 ml of hexane, and the mixture was shaken for 10 minutes 5 ml of the hexane phase was evaporated to dryness. 300 μl of hexane was added to the residue and 25 μl of the resulting solution was used for high performance liquid chromatography. The analytical conditions of high performance liquid chromatography were as follows.

Figure 4:
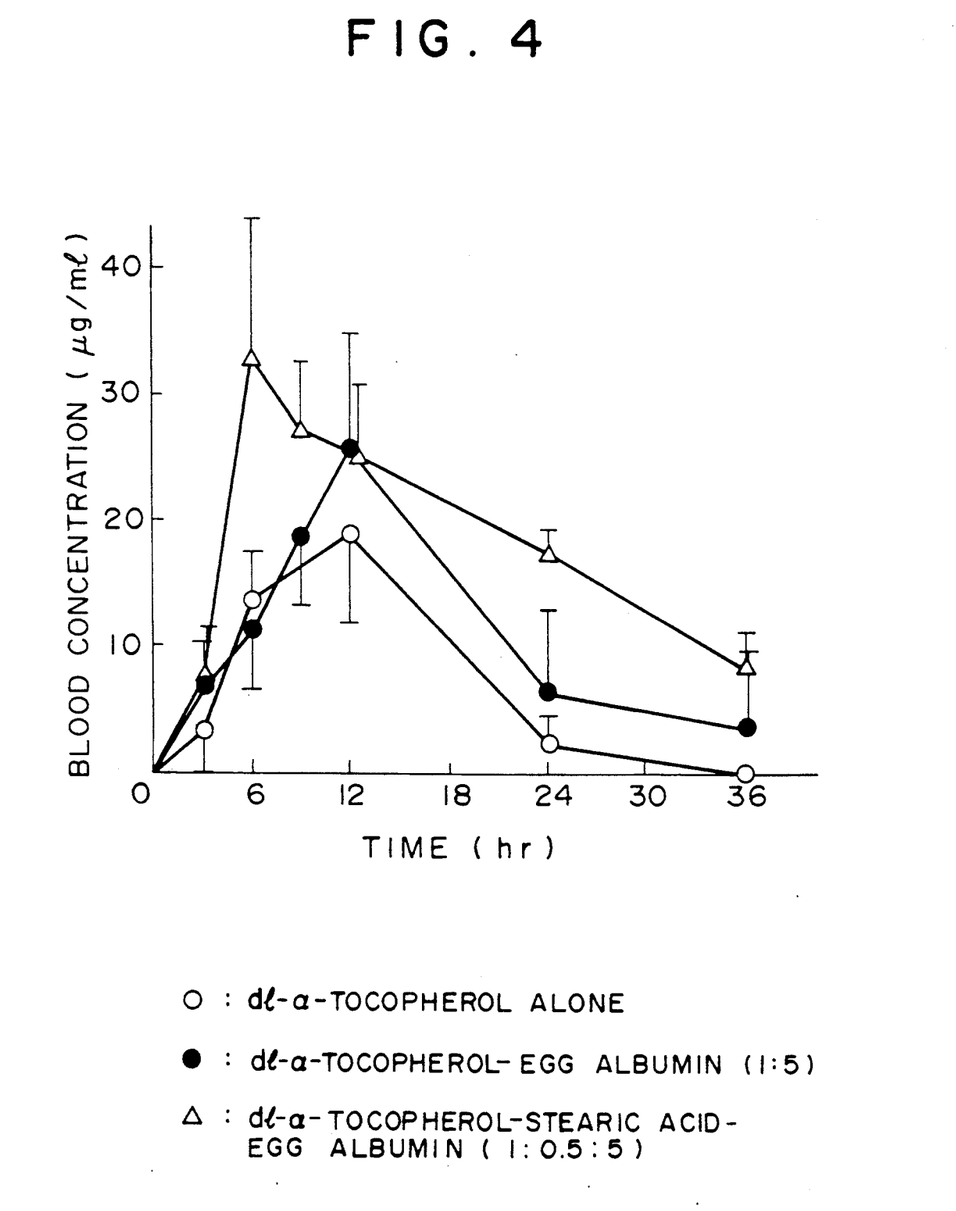
FIG. 4 is a graph showing a change with time of the blood concentration of dl-α-tocopherol after the administration of a dl-α-Tocopherol-egg albumin composition.

Column: Lichrosorb SI-60 (7 μm, 4 mm (inside diameter) x 25 cm (length))
Mobile phase: Hexane: isopropanol =99.5 : 0.5
Flow rate: 1.0 ml/min
Detection wavelength: Excitation wavelength 295 nm
Fluorescent wavelength: 330 nm The results are shown in FIG. 4. In the administration of the dl-α-Tocoherol-egg albumin composition, a rise in blood concentration of dl-α-Tocopherol was observed. The area below the blood concentration-time curve (AUC), of egg albumin : dl-α-Tocopherol : stearic acid (5:1:0.5) increased to 2.8 times that of dl-α-Tocopherol alone, and the area of egg albumin dl-α-Tocopherol (5:1) increased to 1.6 times that of dl-α-Tocopherol alone. The time to the attainment of the maximum blood concentration was as short as 6 hours in the administration of the composition containing stearic acid, as compared with 12 hours in the administration of dl-α-Tocopherol alone. These results indicate that the dl-α-Tocopherol-egg albumin composition has an excellent absorption characteristic.

The production of the pharmaceutical composition of the present invention is described in detail below referring to Examples.

EXAMPLE 1 (NIFEDIPINE-ALBUMIN COMPOSITION)

Figure 3:
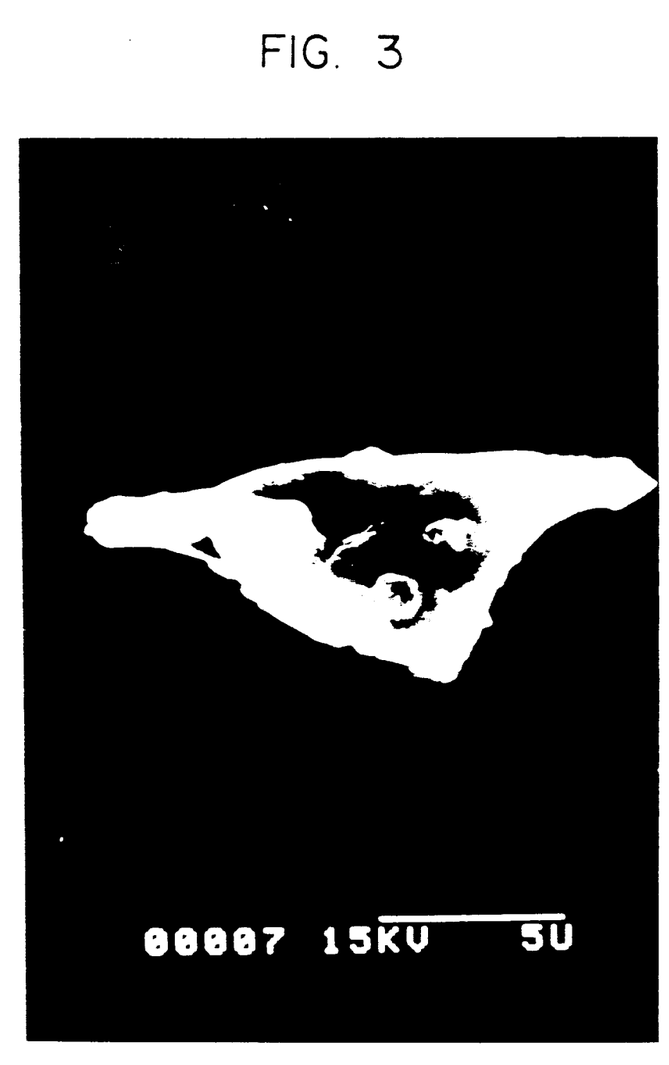
FIG. 3 is a scanning type electron micrograph of the Nifedipine-albumin composition obtained in Example 1.

18 g of egg albumin was added to 400 ml of distilled water. The mixture was stirred at a high speed of about 10,000 rpm using biolyzer (Model BM-4, product of Nihon Seiki Seisakusho) with cooling to obtain a uniform phase. To this uniform phase was added a solution of 2 g of Nifedipine dissolved in 6 ml of acetone The mixture was stirred at a high speed for 1 hour with cooling The resulting uniform suspension was subjected to vacuum distillation to remove the organic solvent. The residue was lyophilized to obtain a powder. This powder was passed through a 100-mesh screen to obtain a Nifedipine-albumin composition having uniform particle diameters. The Nifedipine-albumin composition had a stereostructure of plate crystal having a maximum particle diameter of about 15 $\mu$m, as shown in a scanning type electron micrograph of FIG. 3.

EXAMPLES 2-22

Various drug-albumin compositions in powder form were obtained in the same manner as in Example 1 except that the drugs and solvents shown in Table 4 were used and that the conditions for high speed stirring and drying were varied appropriately depending upon the type, property, etc. of the drug and solvent used.

TABLE 4

| Example No. | Drug, solvent and their amounts used | | | |
|---|---|---|---|---|
| | Drug | (g) | Solvent | (ml) |
| 2 | Aspirin | 2 | Ethanol | 20 |
| 3 | Indometacin | 2 | Ethanol | 20 |
| 4 | Nalidixic acid | 2 | Chloroform | 60 |
| 5 | Piroxicam | 2 | Acetone | 80 |
| 6 | Sulindac | 2 | Methanol | 100 |
| 7 | Phenylbutazone | 2 | Acetone | 10 |
| 8 | Cefaclor | 2 | Distilled water | 100 |
| 9 | Cefalexin | 2 | Distilled water | 100 |
| 10 | Tetracycline hydrochloride | 1 | Ethanol | 100 |
| 11 | Ampicillin | 2 | Distilled water | 100 |
| 12 | Dexamethasone | 1 | Ethanol | 100 |
| 13 | dl-α-Tocopherol* | 3.6 | Acetone | 100 |
| 14 | Haloperidol | 2 | Methanol | 100 |
| 15 | Diltiazem hydrochloride | 2 | Methanol | 50 |
| 16 | Cefalexin | 1 | Distilled water | 100 |
| 17 | Griseofulvin | 2 | Ethanol | 200 |
| 18 | Vincristine sulfate | 2 | Ethanol | 80 |
| 19 | Cimetidine | 2 | Methanol | 60 |
| 20 | Ketotifen | 2 | Methanol | 80 |
| 21 | Glycyrrhizin | 2 | Methanol | 60 |
| 22 | Tranilast | 2 | Acetone | 200 |

*In addition to the dl-α-Tocopherol-egg albumin composition (1:5), there was also produced a composition further containing stearic acid (1.8 g was used), i.e. a dl-α-Tocopherol-egg albumin-stearic acid composition (1:5:0.5).

EXAMPLE 23 (INDOMETACIN-ALBUMIN COMPOSITION)

Figure 5:
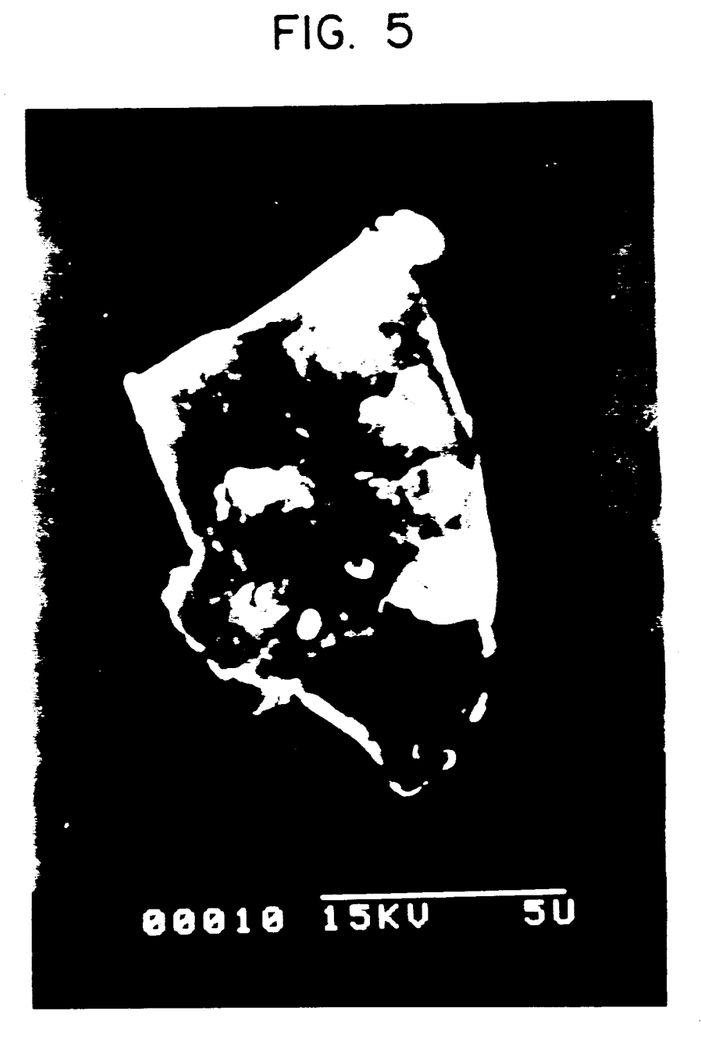
FIG. 5 is a scanning type electron micrograph of the Indometacin-egg albumin composition obtained in Example 23.

3 g of Indometacin was dissolved in 30 ml of ethanol. The solution was added to 600 ml of an aqueous solution containing 5% (w/v) (30 g) of egg albumin. The mixture was subjected to high speed stirring at about 20,000 rpm at room temperature for 30 minutes using a biomixer (Model BM-4, product of Nihon Seiki Seisakusho) to obtain a uniform phase. This uniform phase was treated by an evaporator with keeping at 50-60° C. to evaporate ethanol. The residue was lyophilized to obtain 28.7 g of an Indometacin-egg albumin composition. The Indometacin-egg albumin composition had a stereostructure of plate crystal having a maximum particle size of about 10 $\mu$m, as shown in a scanning type electron micrograph of FIG. 5.

EXAMPLE 24 (INDOMETACIN-ALBUMIN COMPOSITION)

Figure 6:
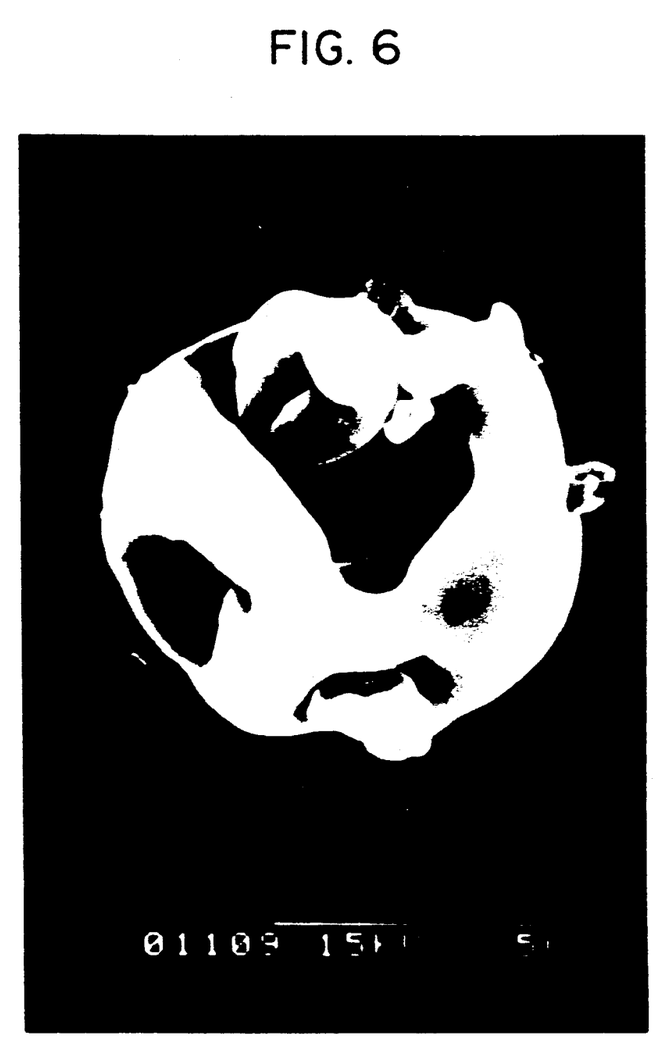
FIG. 6 is a scanning type electron micrograph of the Indometacin-egg albumin composition obtained in Example 24.

3 g of Indometacin was dissolved in about 60 ml of acetone. Thereto was added about 100 ml of olive oil. The mixture was subjected to high speed stirring at about 10,000 rpm for about 30 minutes. Zeolite was added and the whole mixture was heated to about 70-80° C. to evaporate acetone with nitrogen gas being introduced. Separately, 30 g of egg albumin was added to about 900 ml of redistilled water. With ice cooling, the mixture was subjected to high speed stirring at about 10,000 rpm for about 30 minutes using a biomixer (Model BM-4, product of Nihon Seiki Seisakusho) to obtain a uniform phase. The Indometacin-olive oil mixture and the suspension of egg albumin in redistilled water were placed in an eggplant type flask and mixed with shaking. With ice cooling, the mixture was subjected to high speed stirring at about 10,000 rpm for about 2 hours using the biomixer and then to flash drying using a spray dryer (inlet temperature: about 130-140° C., outlet temperature: about 70-80° C.) to obtain 26.5 g of an Indometacin-egg albumin composition. The Indometacin-egg albumin composition had a stereostructure having a shape of connected donuts of 5-10 $\mu$m in average size, as shown in a scanning type electron micrograph of FIG. 6.

EXAMPLE 25 (ASPIRIN-ALBUMIN COMPOSITION)

18 g of egg albumin was added to 400 ml of distilled water. With cooling, the mixture was subjected to high speed stirring at about 10,000 rpm for about 30 minutes using a biomixer (Model BM-4, product of Nihon Seiki Seisakusho) to obtain a uniform phase. Separately, 2 g of Aspirin was dissolved in 20 ml of ethanol. The resulting solution was added to the above uniform phase. With cooling, the mixture was subjected to high speed stirring at about 10,000 rpm for about 1 hour using the biomixer to obtain a uniform suspension. The suspension was subjected to vacuum distillation to remove the organic solvent, and the residue was lyophilized to obtain a powder. The powder was passed through a 100-mesh screen to obtain about 18 g of an Aspirin-egg albumin composition having uniform particle diameters.

EXAMPLE 26 (PHENYLBUTAZONE-ALBUMIN COMPOSITION)

1 g of Phenylbutazone was dissolved in 3 ml of acetone. The solution was added to 200 ml of an aqueous 5% (W/V) egg albumin solution. The mixture was subjected to high speed stirring at about 10,000 rpm for about 30 minutes at room temperature using a biomixer (Model BM-4, product of Nihon Seiki Seisakusho) to obtain a uniform phase. With keeping at 50-60° C., the uniform phase was treated by an evaporator to evaporate ethanol, and the residue was subjected to flash drying using a spray dryer (inlet temperature: about 130-140° C., outlet temperature: about 70-80° C.) to obtain about 9.2 g of a Phenylbutazone-egg albumin composition.

EXAMPLE 27 (PIROXICAM-ALBUMIN COMPOSITION)

18 g of egg albumin was added to 400 ml of distilled water. With cooling, the mixture was subjected to high speed stirring at about 10,000 rpm for about 30 minutes using a biomixer (Model BM-4, product of Nihon Seiki Seisakusho) to obtain a uniform phase. 2 g of Piroxicam was dissolved in 100 ml of methanol and the resulting solution was added to the above uniform phase. With cooling, the mixture was subjected to high speed stirring at about 10,000 for about 1 hour using the biomixer to obtain a uniform suspension. This suspension was subjected to vacuum distillation to remove the organic solvent. The residue was lyophilized to obtain a powder. This powder was passed through a 100-mesh screen to obtain about 18 g of a Piroxicam-egg albumin composition having uniform particle diameters.

EXAMPLE 28 (SULINDAC-ALBUMIN COMPOSITION)

18 g of egg albumin was added to 400 ml of distilled water. With cooling, the mixture was subjected to high speed stirring at about 10,000 rpm for about 30 minutes using a biomixer (Model BM-4, product of Nihon Seiki Seisakusho) to obtain a uniform phase. 2 g of Sulindac was dissolved in 100 ml of methanol. The resulting solution was added to the above uniform phase. With cooling, the mixture was subjected to high speed stirring at about 10,000 rpm for about 1 hour using the biomixer to obtain a suspension. The suspension was subjected to vacuum distillation to remove the organic solvent, and the residue was lyophilized to obtain a powder. This powder was passed through a 100-mesh screen to obtain about 18 g of a Sulindac-egg albumin composition having uniform particle diameters.

Next, there are shown Examples for producing a medicine from the pharmaceutical composition of the present invention.

EXAMPLE 29

| Composition of Example 23 | 50 g |
| --- | --- |
| Lactose | 20 g |
| Corn starch | 20 g |
| Crystalline cellulose | 7 g |
| Hydroxypropyl cellulose | 1 g |
| Magnesium stearate | 1.5 g |
| Talc | 0.5 g |
| | 100 g |

Procedure

There were mixed the composition of Example 23, lactose, corn starch and crystalline cellulose. To this mixture was added a solution of hydroxypropyl cellulose dissolved in 30 ml of water, and they were kneaded sufficiently. The mixture was granulated and dried. The resulting granules were mixed with magnesium stearate and talc and then made into tablets each of 200 mg.

EXAMPLE 30

| Composition of Example 24 | 400 g |
| --- | --- |
| Lactose | 300 g |
| Potato starch | 270 g |
| Hydroxypropyl cellulose | 30 g |
| | 1,000 g |

Procedure

The composition of Example 24, lactose and potato starch were mixed. To this mixture was added a solution of hydroxypropyl cellulose dissolved in 400 ml of water, and they were kneaded sufficiently. The mixture was granulated and dried. The resulting granules were made uniform to obtain granules.

EXAMPLE 31

| Composition of Example 25 | 2,500 g |
| --- | --- |
| Lactose | 400 g |
| Hydroxypropyl cellulose | 100 g |
| | 3,000 g |

Procedure

The composition of Example 25 and lactose were mixed. To this mixture was added a solution of hydroxypropyl cellulose dissolved in 1,000 ml of water, and they were kneaded sufficiently. The mixture was granulated and dried. The resulting granules were made uniform to obtain granules.

EXAMPLE 32

| Composition of Example 27 | 100 g |
| --- | --- |
| Lactose | 200 g |
| Potato starch | 50 g |
| Crystalline cellulose | 46 g |
| Magnesium stearate | 4 g |
| | 400 g |

Procedure

The above components were mixed sufficiently. 400 mg of the resulting mixture was filled into a No. 0 capsule to obtain capsules.

As described above in detail, the pharmaceutical composition of the present invention is a drug-albumin composition wherein albumin as a carrier supports a high concentration of a drug by forming a hydrophobic bonding with the drug, and exhibits excellent effects such as the alleviation of the drug's side effect undesirable to the human body, the improvement of the absorption and light stability of the drug and the like. Since the present composition contains a drug in a high concentration, the composition has a further advantage of being applied even to drugs of high administration dosage.

The process of the present invention for producing the pharmaceutical composition having the above advantages is a very simple process comprising subjecting a drug and albumin to high speed stirring in an aqueous solvent and then removing the solvent. It has a very high industrial significance in that the procedure is simple.

I claim:

1. A process for producing a pharmaceutical composition comprising mixing together at high speed in a solvent 1 to 250 parts by weight of a drug capable of binding to protein and 100 parts by weight of albumin, and thereafter (2) removing the solvent, wherein the drug is nifedipine, aspirin, nalidixic acid, piroxicam, sulindac, phenylbutazone, cefaclor, cefalexin, tetracycline hydrochloride, ampicillin, dexamethasone, dl-α-tocopherol, haloperidol, diltazem hydrochloride, defalexin, griseofulvin, vincristine sulfate, cimetidine, ketotifen, glycyrrhizin or tranilast.

2. A process according to claim 1, wherein the amount of the drug is 5–200 parts by weight.

3. A process according to claim 1, which further uses a fatty oil and/or a fatty acid.

4. A process according to claim 1, wherein the aqueous solvent is water or a mixture of water and an organic solvent.

5. A process according to claim 3, wherein the drug is dissolved in the fatty oil and/or the fatty acid in the presence of an organic solvent if necessary and then the resulting solution is added to an aqueous suspension of natural albumin.

6. A process according to claim 1, wherein the stirring is effected at a high speed of 5,000–40,000 rpm.

* * * * *